United States Patent [19]

Mendelson

[11] Patent Number: 5,599,988
[45] Date of Patent: Feb. 4, 1997

[54] LARGE SCALE PREPARATION OF 2,4-DIHYDROXYBENZALDEHYDE USING A VARIATION OF THE VILSMEIER–HAACK REACTION AND ISOLATED INTERMEDIATES

[75] Inventor: Wilford Mendelson, King of Prussia, Pa.

[73] Assignee: SmithKline Beecham Corporation, Philadelphia, Pa.

[21] Appl. No.: 362,730

[22] Filed: Dec. 22, 1994

[51] Int. Cl.$^6$ .................... C07C 249/00; C07C 45/00; C07C 45/90
[52] U.S. Cl. ................ 564/272; 568/436; 568/437
[58] Field of Search ........................ 568/425, 436, 568/437; 564/272

[56] References Cited

U.S. PATENT DOCUMENTS

| | | | |
|---|---|---|---|
| 1,807,693 | 6/1931 | Kalischer et al. | 568/436 |
| 3,453,286 | 7/1969 | Sungawa et al. | 564/272 |
| 4,024,274 | 5/1977 | Druckrey et al. | 564/272 |
| 4,157,333 | 6/1979 | Nakatani et al. | 549/436 |
| 4,808,711 | 2/1989 | Shimizu et al. | 540/227 |

FOREIGN PATENT DOCUMENTS 7089891 4/1995 Japan.

OTHER PUBLICATIONS

Mendelson et al.,"Preparation of 2,4–Dihyroxybenzaldehyde by the Vilsmeier–Haack Reaction," *Synthetic Comm.*, 26(3), 603–610 (1996).
Weygand & Hilgetag, *Preparative Organic Chemistry*, Hilgetag & Martini (eds.), John Wiley & Sons, New York, 1972, pp. 924, 926 and 974–977 only.
Ferguson, "The Synthesis of Aromatic Aldehydes," *Chemical Reviews*, 38(2), 277–254, 1946; see particularly § D, pp. 230–231.

Richter (ed.), *Beilsteins Handbuch der Organischen Chemie, Part. 4 of the Second Treatise*, Springer–Verlag, 1944, Berlin, Germany, System. No. 554, see p. 810, see lines 7–8.
H–G Boit (ed.), *Beilsteins Handbuch der Organischen Chemie, Part. 4 of the Third Treatise*, Springer–Verlag, 1967, Berlin, Germany, System. No. 554, see p. 4299, paragraph 4, last sentence.
Carvalho et al., "Boron Trichloride as a Selective Demethylating Agent for Hindered Ethers: A Synthesis of the Phytoalexins a– and β–Pyrufuran, a Synthesis of Tri–O–Methylleprolomin and Its Demethlation", *Australian J. of Chemistry*, 38(5), 777–792 (1985).
Barnett et al., "Pyrrole Chemistry. XXI. Synthetic Approaches to Cyanopyrroles," *Canadian J. Chemistry*, 58(4), 409–411 (1980).
Fieser et al. (I), *Reagents for Organic Synthesis*, vol. 1, John Wiley & Sons, 1967, New York, NY, pp. 284–285 & 770–771 only.
Fieser et al. (II), *Reagents for Organic Synthesis*, vol. 5, John Wiley & Sons, 1975, New York, NY, p. 249 only.
M. Fieser, *Fieser & Fieser's Reagents for Organic Synthesis*, vol. 12, John Wiley & Sons, 1986, New York, NY, p. 201 only.

*Primary Examiner*—John Kight
*Assistant Examiner*—L. Eric Crane
*Attorney, Agent, or Firm*—Dara L. Dinner; Stephen Venetianer; Edward T. Lentz

[57] ABSTRACT

A novel process for producing chiral hydroxylamines for use as intermediates to make chiral hydroxyureas, which process comprises a tandem condensation-cyclization reaction between a dimethylsulfoxonium methylide and an appropriately substituted nitrone bearing a D- or L- mannose chiral auxiliary to yield a compound of Formula (I) as claimed herein.

4 Claims, No Drawings

LARGE SCALE PREPARATION OF 2,4-DIHYDROXYBENZALDEHYDE USING A VARIATION OF THE VILSMEIER–HAACK REACTION AND ISOLATED INTERMEDIATES

FIELD OF THE INVENTION

Enantioselective synthesis of chiral intermediates and final N-hydroxyurea containing products.

BACKGROUND OF THE INVENTION

The general literature for an enantioselective synthesis for chiral intermediates and final products containing hydroxylamines, hydroxamate or hydroxyurea functionalities is quite limited. Obtainment of either desired configuration (i.e., (R) or (S)) occurs primarily by three routes, 1) resolution, 2) separation of a racemic mixture by derivatization and separation means, such as by column chromatography, or 3) by enantioselective synthesis.

For hydroxyurea containing compounds a synthesis has been described in patent application WO 91/14674, published 10.03.91 to Adams et al. which teaches obtainment of the chiral hydroxylamine, which upon appropriate work-up results in a chiral final product. This method is not, however, commercially feasible, due to excessive costs in obtaining the chiral intermediate by the processes indicated therein.

Primarily, the work in the past to achieve chiral compounds, lies in the use of nucleophilic additions to chiral nitrones. These chiral nitrones, bear various auxiliaries, (such as sugars or other chiral moieties) giving a non-racemic environment for nucleophilic addition or dipolar cycloaddition reactions. Various allylic Grignard reagents have generally been used in these reactions. For instance, Schwartz et at., Tet. Lett., 34, p 1011 (1993) employs a nucleophilic addition to a sugar based chiral nitrone for an enantioselective formation of a chiral hydroxylamine and uses a gulose based sugar and Grignard reagents as the nucleophile. To achieve a high level of enantioselectivity, co-addition of trimethylaluminum, a hazardous agent, is required.

Mancini et at., J. Org. Chem., 56, p 4246-252 (1991) also describes a chiral hydroxylamine synthesis using as a chiral auxiliary, a sugar moiety which is mannose derived. Mancini et al., requires adding an allyl Grignard reagent to the nitrone bearing sugar molecule which after reactoion with an O-trialkylsilyl reagent and treatment with an iodinating agent cyclize to an isoxazolidine compound.

Huber etal., Helv. Chim. Acta, 68, 1730 (1985) describes both the diasterioselective 1,3-dipolar cycloadditions of N-glycosylnitrones to methyl methacrylate to afford N-glycosylisoxazolidines and the diastereoselective nucleophilic addition of lithium and potassium dialkylphophites to N-glycoxylnitrones to yield N-glycosyl-N-hydroxyaminophosphonates.

The use of trimethylsulfoxonium iodide and potassium tert-butoxide (in DMSO) have previously been shown by Ng, J., Synthetic Comm., 20(8), 1193–1202 (1990), to prepare epoxides from aldehydes and ketones. Previously the most common method to prepare epoxides from aldehydes and ketones involved the use of methyloxosulfonium and methylsulfonium methylides developed by Corey et al., J. Am. Chem.Soc, 84, 867 (1962); and J. Am. Chem. Soc., 87, 1353 (1965). For an additional review of dimethylsulfoxonium methylide see Golobobov et al., Tetrahedron, 43, 2609 (1987). Holt et al., Tetrahedron Letters, 7,683-686 (1966) describe the reaction of dimethylsulphoxonium methylide with ortho-hydroxy aldehydes to yield hydroxy substiututed benzofuran derivatives as described therein.

The use of these reagents as applied to chiral nitrones for intramolecular cyclization of heterocylic rings, such as benzo[d]furan heterocycles, from a chiral mannose nitrone intermediate, as described in the present invention, is novel and suitable for large scale commercial processes.

There exists a need, in this art, to provided a highly diasteroselective synthesis for hydroxylamine intermediates which resulting product has a high optical purity and can be done is a single stage. Preferably, the resultant synthesis should also allow regeneration and recovery of the chiral auxiliary to reduce synthesis costs.

SUMMARY OF THE INVENTION

The present invention is a highly selective diastereomeric synthesis of a chiral hydroxylamine and a resultant chiral final product, such as a hydroxyurea or hydroxamate derivative thereof. This is accomplished by the novel use of an ylide and a nitrone bearing a mannose based chiral auxiliary which upon cleavage then affords the chiral hydroxylamine. This invention entails the tandem addition-cyclization of chiral nitrones of ortho hydroxy benzaldehydes with methylsulfoxonium ylides.

In particular, the present invention is to an enantioselective preparation of a dihydrobenzofuran substituted hydroxylamine. Further, if the resultant product has a phenolic ortho-substituent it will undergo an intramolecular cyclization with elimination of a neutral thioether, such as DMSO, leading to a benzodihydrofuran derivative. This reaction creates in a single step, with high purity, a 2,3-dihydrobenzo[d]furan heterocycle which has a chiral hydroxylamine substituent. In particular, the ylide is a thioylide, such as dimethylsulfoxonium methylide.

The present invention is also to a highly efficient, high yield regioselective synthesis to a chemical intermediate in the above noted process, a 4-benzyloxy-2-hydroxy-benzaldehyde compound. Regioselective benzylation of 2,4-dihydroxybenzaldehyde is obtained by the novel use of dry potassium fluoride and benzyl chloride in acetonitrile or alternatively with $NaHCO_3$ and KI in acetonitrile.

DETAILED DESCRIPTION OF THE INVENTION

The present invention is to a highly efficient, high yield enantioselective preparation of a dihydrobenzofuran substituted hydroxylamine compound of Formula (I). Such a reaction, it has been found, occurs when a chiral nitrone which is prepared from a hydroxylamine intermediate bearing a chiral sugar auxiliary, such as a D- or L- mannose, and an appropriately substituted carboxyaldehyde, each undergo a highly diastereoselective condensation with an appropriate nucleophile. The D-or L- mannose derived auxiliary is readily removed, and optionally recycled, thus unraveling the chiral hydroxylamine in very high enantiomeric excess, and providing reduced costs for the entire process by reuse of the mannose auxiliary (or sugar).

While it is recognized that the mannose-hydroxylamine, the resulting nitrone, and cyzlized rings, may bear any chiral sugar auxiliary, not just a D or L- mannose, preferably D-mannose, for purposes herein the schemes will generically refer to mannose, Compounds of Formula (I) have the following structure:

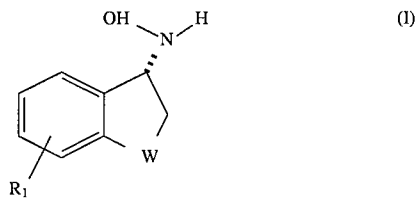

wherein $R_1$ is hydrogen, $alkyl_{1-10}$, $alkoxy_{1-10}$, $(CH_2)_m\text{-Ar-}(X)_v$, $O(CH_2)_m\text{-Ar-}(X)_v$, or $S(CH_2)_m\text{-Ar-}(X)_v$;

W is $CH_2(CH_2)_s$, $O(CH_2)_s$, $S(CH_2)_s$, or $NR_7(CH_2)_s$;

$R_7$ is hydrogen, $C_{1-4}$ alkyl, or phenyl;

s is a number having a value of 0 to 3, m is a number having a value of 0 to 3;

v is a number having a value of 0 to 3;

Ar is a member selected from the group consisting of phenyl, napthyl, quinolyl, isoquinolyl, pyridyl, furanyl, imidazoyl, benzimidazolyl, triazolyl, oxazolyl, isoxazolyl, thiazole,or thienyl;

X is a member selected from the group consisting of hydrogen, halogen, $alkyl_{1-5}$, $cycloalkyl_{5-8}$, hydroxy, $(CHY)_t$carboxy, $O\text{-}alkyl_{1-5}$, $S(O)_r alkyl_{1-5}$, halosubstituted $alkyl_{1-6}$, $(CHY)_tN(R_5)_2$ or cyano;

r is a number having a value of 0 to 2;

Y is hydrogen or $alkyl_{1-3}$;

$R_5$ is H or $alkyl_{1-6}$;

t is a number having a value of 0 or 1.

The mannose hydroxylamine derivative 3-Scheme-1, used herein, may be synthesized by art recognized means such as those indicated in the synthesis below for Scheme I, or as in the working Examples herein. The desired sugar, in this instance, D-mannose 1-Scheme-1 is reacted in DMF or acetone with dimethoxypropane, and p-toluenesulfonic acid (at about 70° to about 80° C. for about 1 hour) to yield the diacetonide 2-Scheme-1 compound to which hydroxylamine hydrochloride is added, in NaOH solution, for about 1 hour at about 80° to 90° C., producing the mannose oxime/hydroxylamine 3a/b-Scheme-1, alternatively, ethanol, THF or ethyl acetate may be used as a solvent in the second step and sodium acetate or sodium bicarbonate may used in place of sodium hydroxide. The oxime 3a is present in a significant excess to the hydroxylamine 3b, and for purposes herein the structures may be used interchangeably in the schemes. It is also possible to run this reaction as a two-step two-pot synthesis isolating the intermediate 2-Scheme 1, but this is cosily in time and inefficent throughput.

Scheme I

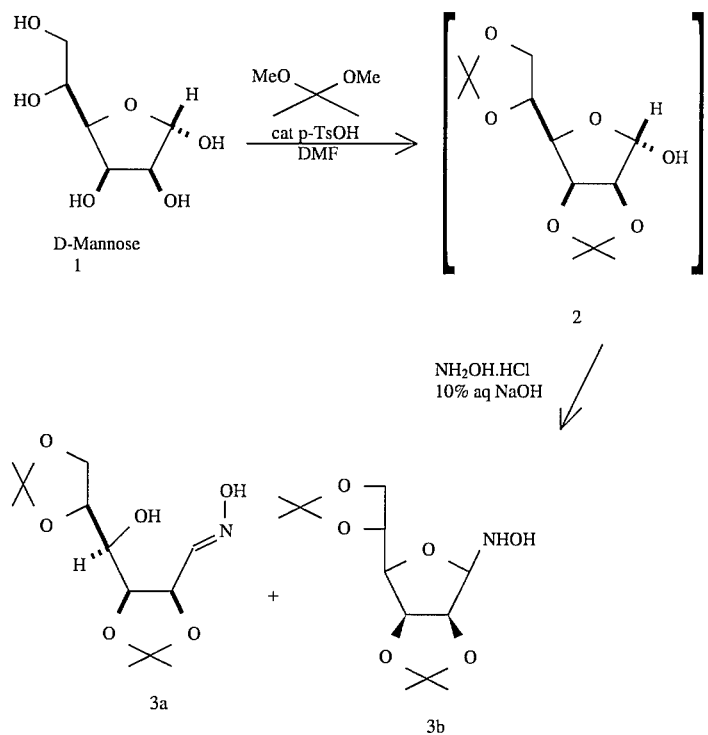

In Scheme II below, a chiral nitrone 4-Scheme-2 is prepared from the mannosehydroxylamine 3-Scheme-1 using an appropriate aldehyde, RCHO which is then reacted with an appropriate nucleophile and finally the mannose is removed to yield a desired enantiomeric hydroxylamine intermediate.

Scheme II

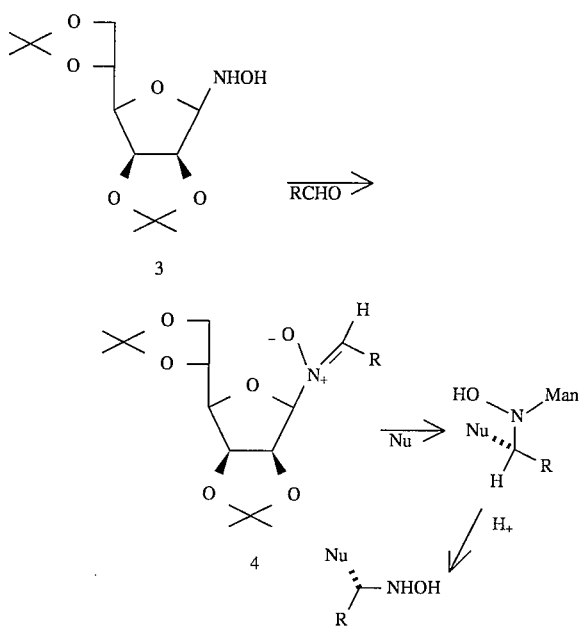

A suitable aldehyde (RCHO) for use herein is an aldehyde having the formula:

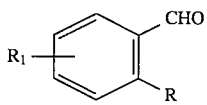

(A)

wherein

R is OH, SH or $NR_7$;

$R_7$ is hydrogen, $C_{1-4}$alkyl, or phenyl;

$R_1$ is hydrogen, $alkyl_{1-10}$, $alkoxy_{1-10}$, $(CH_2)_m\text{-Ar-}(X)_v$, $O(CH_2)_m\text{-Ar-}(X)_v$, or $S(CH_2)_m\text{-Ar-}(X)_v$;

X is independently selected from hydrogen, halogen, $alkyl_{1-5}$, $cycloalkyl_{5-8}$, hydroxy, $(CHY)_r$carboxy, O-alkyl $_{1-5}$, $S(O)_r alkyl_{1-5}$, halosubstituted $alkyl_{1-6}$, $(CHY)_t N(R_5)_2$ or cyano;

$R_5$ is independently hydrogen or $alkyl_{1-6}$;

Ar is a member selected from the group consisting of phenyl, napthyl, quinolyl, isoquinolyl, pyridyl, furanyl, imidazoyl, benzimidazolyl, triazolyl, oxazolyl, isoxazolyl, thiazole,or thienyl;

m is a number having a value of 0 to 3;

v is a number having a value of 0 to 3;

r is a number having a value of 0 to 2;

Y is hydrogen or $alkyl_{1-3}$; and t is a number having a value of 0 or 1.

For compounds of Formula (A), R is preferably OH. If the Ar ring is substituted more than once it is preferable that at least one substituent be selected from halogen, halosubstituted $alkyl_{1-6}$, alkyl, or O-$alkyl_{1-5}$. Preferably, the Ar is phenyl or napthyl, more preferably phenyl, and m is preferably 0, 1 or 2; more preferably 1. Preferably the Ar group is unsubstituted or substituted one to three times independently by halogen, trifluoromethyl or combinations thereof. Preferably, the halogen is fluorine, or chlorine, or combinations thereof, more preferably fluorine. Most preferred is the 2,6-difluoro substitution.

Preferably $R_1$ is $O(CH_2)_m\text{Ar-}(X)_v$; Ar is phenyl, and m is preferably 0, 1 or 2; more preferably 1; and X is preferably hydrogen, halogen, or halosubstituted $alkyl_{1-6}$; more preferably the aryl ring is unsubstituted or substituted one to three times independently by fluorine, chlorine, triflurom-ethyl or combinations thereof. Preferably, the phenyl is difluoro substituted, and specifically in the 2,6-position.

In a preferred aspect of the present invention, a suitable aldehyde, such as an optionally substituted benzaldehyde may be prepared as described in Scheme 3 below. The benzylaldehyde of 6-Scheme-3 is available commercially or may be prepared by well known literature references, such as Gross etal., Chem. Ber. 1963, 96, 308–313. This aldehyde is a key intermediate in the asymmetric synthesis of the final products. The chirality of the hydroxyureas is derived from the nitrone condensation product of the aldehyde with a mannose derivative. Compound 5-Scheme-3 is converted to it's protected form, the optionally substituted benzaldehyde derivative 6-Scheme-3 which is then reacted via the mannose-nitrone route indicated in the Schemes 1 and 8 herein.

Scheme 3

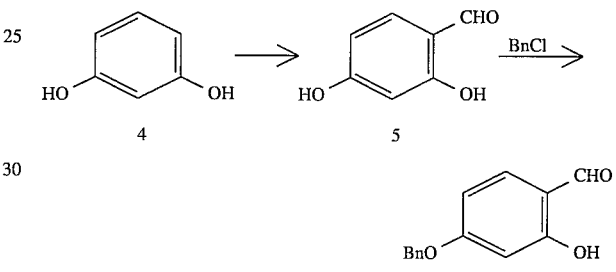

The aldehyde, 5-Scheme 3, in another aspect of the present invention may also be produced using a Vilsmeier formylation of resorcinol with either phosphorous oxychloride/DMF or oxalyl chloride/DMF in acetonitrile at below room temperature, using resorcinol as a starting material in good yield and high purity.

These methods have advantages over Nenitzescu, et al. Chem. Abst. 1930, 24, 2442 formylated resorcinol in an ether solution with oxalyl chloride-formamide and produced 1-Scheme 4 via a crystalline intermediate in an unspecified yield. The reaction however produced mixtures, and the aldehyde in low yield, as well as using diethyl ether. Recently Downie, et al., *Tetrahedron* 1993, 49, 4015 used pyrophosphoryl chloride and DMF to efficiently formylate resorcinol as well as many heterocyclic systems. The expense and unavailability of pyrophosphoryl chloride for large scale work, as well as the ecological undesirability, renders this synthesis not commerically feasible. The novel use of activating agents phosphoryl chloride and oxalyl chloride, both readily available in large quantires, is a key feature to the usefulnes of this reaction. Generally, older methods for carrying out similar formylations use hazardous solvents, such as ether, as well as toxic reagents. The present method utilizes inexpensive, generally safe, commerically available reagents.

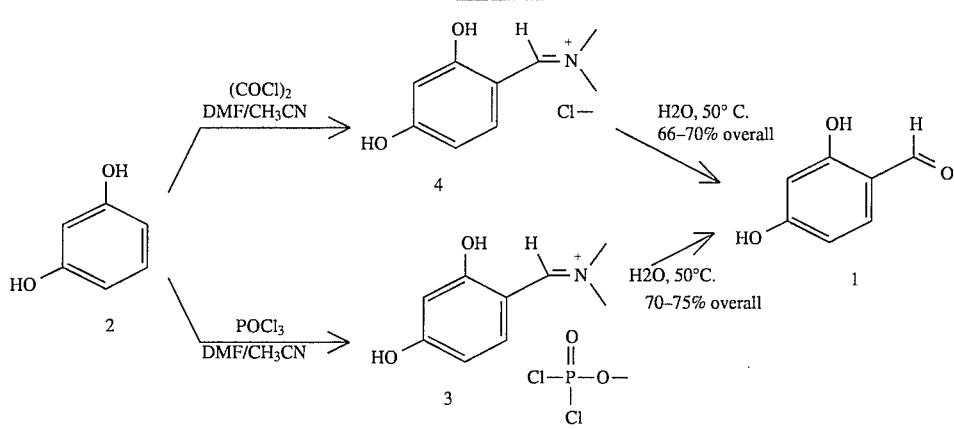

Scheme 4

In the first example, the Vilsmeier reagent is prepared by the addition of POCl₃ in acetonitrile to DMF in the same solvent at room temperature. The reaction is then cooled to about −15° C., resorcinol in acetonitrile is added, and after about 2 hours the reaction is warmed to 28°–30° C. The crystalline Vilsmeier-formamidinium phosphorodichloridate salt is isolated by filtration, in a high state of purity in about 75-80% yield. The optimum temperature range is about −10° to about 25° C. during the addition of resorcinol to the Vilsmeier reagent; and the reaction may be compeleted from about 25° to about 50° C. Customarily, for this reaction, for rescorinol about 7 to 12 parts of acetonitrile are used, and from about 1 to 1.5 equivalents of DMF, and about 1 to 1.5 equivalents of POCl₃ are used. Isolation of this novel intermediate salt 3-Scheme 4 provides a simple, convenient means of purification useful in application to large scale work. The salt is stable for several weeks in the dark at −10° C., but it acquires a pink color on standing in the laboratory at ambient temperature for 2–3 days.

The intermediate salt is readily convened to aldehyde 1-Scheme 4 by treatment with water at about 50° C. The desired aldehyde is isolated by precipitation directly from the aqueous solution as a single component in 70–75% overall yield. The conversion can be monitored by NMR by adding D₂O to a sample of 3-Scheme 4 in DMSO-$d_6$. The use of low temperatures of the reaction (−25° to 10° C.) prevents side reactions of resorcinol with the Vilsmeier reagent. Further, isolation of the intermediate formamidinium salt provides a convenient means of purification.

Therefore, another aspect of the present invention is the novel process of using POCl₃ in acetonitrile and DMF to yield the novel formamidinium phosphorodichloridate salt as an isolable intermediate, which upon the addition of water forms 2,4-dihydroxybenzylaldehyde.

Similar results are obtained using the oxalyl chloride-DMF Viismeier reagent as also indicated in Scheme 4. In this case the Vilsmeier reagent, [H(Cl)C=N(CH₃)₂]⁺Cl⁻, precipitates from acetonitrile as a thick solid, and more dilute reactions are used to achieve efficient stirring. The reagent subsequently dissolves as resorcinol is added at about −15° C.; and the novel formamidinium chloride salt 4-Scheme 4 precipitates from the reaction. This salt is converted to 2,4-dihydroxybenzaldehyde on crystallization from warm water in an overall yield of about 69–70% from resorcinol. The employment of acetonitrile and low temperatures during the Vilsmeier coupling are important factors in these high throughput, cost-effective preparations of 1-Scheme 4.

Therefore, another aspect of the present invention is the novel process of using oxalyl chloride in acetonitrile and DMF with resorcinol to yield the novel formamidinium chloride salt as an isolatable intermediate, which upon the addition of water forms 2,4-dihydroxybenzylaldehyde.

The oxalyl chloride and POCl₃ in combination with DMF or N-methyl formanilide are also useful to produce other aromatic aldehydes which are presently synthesized by the Gatterman reaction, the use of HCN or cyanide salts can thus be avoided. "The Gatterman Synthesis of Aldehydes", Organic Reaction, Vol. 9, pp 37–72 (1957). Further, the method will also be useful where the product aldehyde is a liquid; the isolation of the formamidinium salt provides a convenient means of purification, avoiding fractional distillation. The use of oxalyl chloride also provides an alternative to the phosphorous containing reagents and the disposal of phosphorous containing waste streams.

Scheme 5

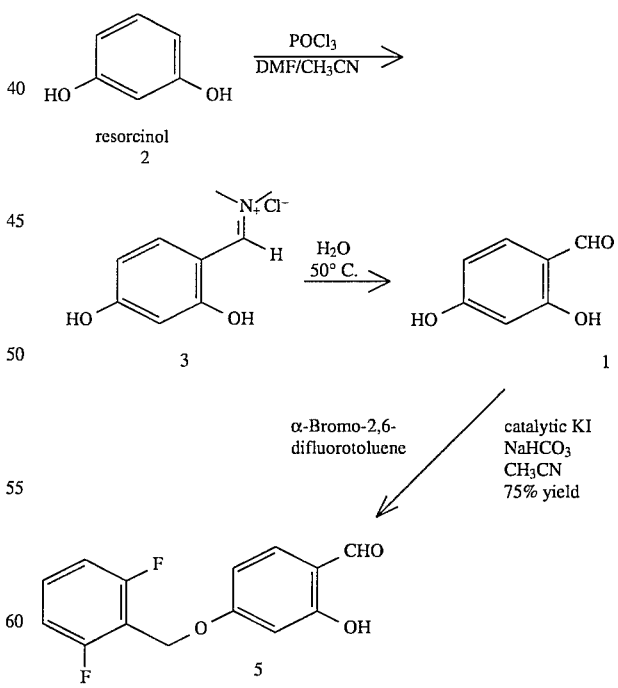

Production of the 2-hydroxy-4-(2',6'-difluorobenzyloxy)-benzaldehyde, 1-Scheme 5 is not problem free. To obtain the selectivel benzylation of the 4-position of the 2,4-di-hydroxybenzaldehyde, one must avoid the random 2-and 4-hydroxyl benzylation and halt the reaction after one benzyl group has been introduced.

Therefore, another aspect of the present invention provides for a process which allows for the alkylation of 2,4-dihydroxybenzaldehyde to give a crude yield of about 75–80% and an isolated yield of pure product greater than 70%. Previously known methods of alkylation fail to give the desired product in more than a 40–45% yield, and many times, chromatography is necessary to obtain the pure product, resulting in a very inefficient method of producing a key intemediate.

For example, reaction of 2-Scheme 5 with potassium or sodium hydroxide in aqueous alcohol in combination with benzyl halide give a poor conversion with 20–45% of the starting material remaining, and 8–20% of the bis-benzyl compound produced. Sodium hydride/DMF in combination with benzyl bromide give 17 to 25% starting material even though 3 equivalents of base and 1.5 equivalents of benzyl bromide were used for extended reaction periods. Likewise, benzyl chloride gave poor results as well. Other bases, such as methyl magnesium bromide, di-isopropyl ethylamine, and Triton B also give unsatisfactory yields.

Use of dry potassium fluoride in combination with benzyl bromide in DMF showed little selectivity. These reaction conditions produced more than 20% of the bis-benzylation product even though significant amounts of starting material were still present in the reaction mixture. Thus, the novel use of the specific combination of dry potassium fluoride, benzyl chloride in acetonitrile, is essential to the sucessful monoalkylation of 2,4-dihydrobenzylaldehyde to produce, for example a 4-(2,6-di-fluorobenzyloxy)-2-hydroxy-benzaldehyde.

Dewick, P. M. *Synth. Commun.* 1981, 11, 853 reported the preparation of 1-Scheme 6 by benzylation of 2-Scheme 6 with benzyl Tosylate ($K_2CO_3$, acetone), but obtained only a 24% yield for the conversion. The procedure of Daly et. at., *J. Am. Chem. Soc.* 1963, 83, 4787 reported that treatment of 2,4-dihydroxybenzaldehyde 2-Scheme 6 with sodium hydroxide (1 equivalent) and benzyl chloride results in selective formation of 1-Scheme 6 in 64% yield. This procedure was repeated several times with disappointing results. In each case the product isolated was in 40–50% yield, mp 73°–76° C., contaminated with starting material (10–15%) and the bis-benzyloxy side product 3-Scheme 6 (Reimann E. *Chem. Ber.* 1969, 102, 2881) (15–20%) (HPLC, percent area response (PAR)). A standard-based HPLC assay of the isolated solid gave a purity figure of ~70%. Thus, the corrected yield of 1-Scheme 6 was less than 35%. Nevertheless, purification of these reaction products by flash-column chromatography provided supplies of the monobenzyl compound 1-Scheme 6 in >95% purity (mp 78°–80° C.), albeit in 25–30% overall yield. Since these yields were too low to provide the compound in a cost-effective manner, reaction conditions were sought that would produce 1-Scheme 6 from 2-Scheme 6 in satisfactory yield and purity.

Scheme 6

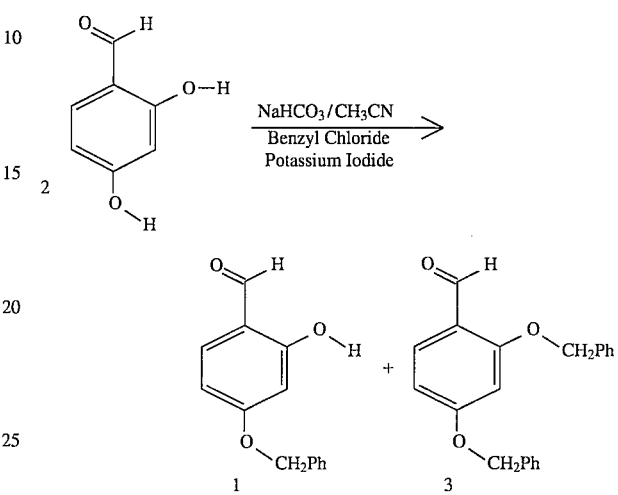

Application of organic bases such as triethylamine, pyridine, or DABCO in combination with benzyl bromide resulted in recovered starting material. Even the use of a stronger base, sodium hydride, (benzyl bromide in DMF solution) results in incomplete reactions of 2-Scheme 6, i.e. less than 45% conversion to product mixtures. The first promising reaction conditions (~50% HPLC area response of 1-Scheme 6) (entry 1, Table I), was realized using 1 equivalent of powdered $K_2CO_3$ in acetone at 40°–80° C. with 1.3 equivalents of benzyl chloride in the presence of a small amount of potassium iodide (0.1–0.2 eq.). It was found that iodide was necessary for success of this reaction; in the absence of potassium iodide reflux for 18 hours resulted in only 16% conversion of starting material (entry 2). The use of acetonitrile as the solvent produced a significant increase in the selectivity of the reaction. Thus, when acetone was the solvent (entry 3), about 25% of the reaction product was the bis-alkylation product 3-Scheme 6. In contrast, using acetonitrile as solvent reduced the amount of this side product to only 12% (entry 4).

TABLE I

| | Preparation of 4-benzyloxy-2-hydroxybenzaldehyde; HPLC of Reaction Solution | | | | | | |
|---|---|---|---|---|---|---|---|
| Entry | Base Used | Alkylating Agent | Solvent | Temp (°C.) or reflux (R) | St. Mat. Area % | Mono-benzyl Area % | Bis-benzyl Area % |
| 1 | $K_2CO_3$ (1.0 eq) | BnCl(I⁻) | Acetone | 40°=>R | 0.2 | 51 | 49 |
| 2 | $K_2CO_3$ (1.0 eq) | BnCl | Acetone | R | 84 | 12 | 4 |
| 3 | $K_2CO_3$ (1.15 eq) | BnCl(I⁻) | Acetone | 40° | 8 | 65 | 25 |
| 4 | $K_2CO_3$ (1.15 eq) | BnCl(I⁻) | $CH_3CN$ | 40° | 6 | 80 | 12 |
| 5 | $NaHCO_3$ (1.15 eq) | BnCl(I⁻) | $CH_3CN$ | R | 5 | 89 | 5.7 |
| 6 | KF (2.0 eq) | BnCl | $CH_3CN$ | R | 8 | 85 | 7 |

When sodium bicarbonate, a weak base, was used as shown in entry 5 in Table 1 above, an 89% conversion to 1-Scheme 6 (PAR via HPLC) was obtained after 16 hours at reflux. The compound was isolated, and after crystallization, gave 68–70% of the desired product (top 76°–78° C.) with an HPLC assay figure (relative to an analytically pure reference) of >92%. A second practical approach to selective alkylation is shown in entry 6, in which anhydrous KF in acetonitrile was used.

The use of alkali metal fluorides in hydrogen-bond assisted reactions of phenols has been well studied by Clark and Miller, Miller et al, *Can. Jour. Chem.*, 1979, 57, 1887; see also Miller et al, *J. Am. Chem. Soc.* 1977, 99, 498; as well as Ishikawa et al, *Chem. Lett.* 1981, 761. Sinhababu, et al, *Tetrahedron Lett.* 1987, 28, 4139 reported the conversion of bis-TBDMS ethers of resorcinol aldehyde to bis-benzyl ethers using fluoride ion, but he made no attempt to prepare mono-benzyl resorcinol derivatives.

It has now been found that KF (2 eq.) and benzyl chloride (1.75 eq.) in refluxing acetonitrile is a very efficient base-solvent combination for use in this reaction. Thus, in this case, excellent conversion to product is attained without iodide activation of benzyl chloride, although the chloride is usually unreactive in phenol benzylations without added iodide.

Other simple ortho-substituted benzyl halides have been successfully used as electrophiles in the benzylation. Table II summarizes these results using substituted benzyl halides (yields are not optimized). In the case of the 2,6-difluorobenzyl bromide (4A-Scheme7) the reaction produced more of the bis-benzylation side product, and the 53% product yield of 5A-Scheme 7 represents losses which occur during a second recrystallization. It cannot be stated whether this loss of regioselectivity is primarily due to the 2,6-disubstitution of fluorine or the fact that bromine is the displaceable halide.

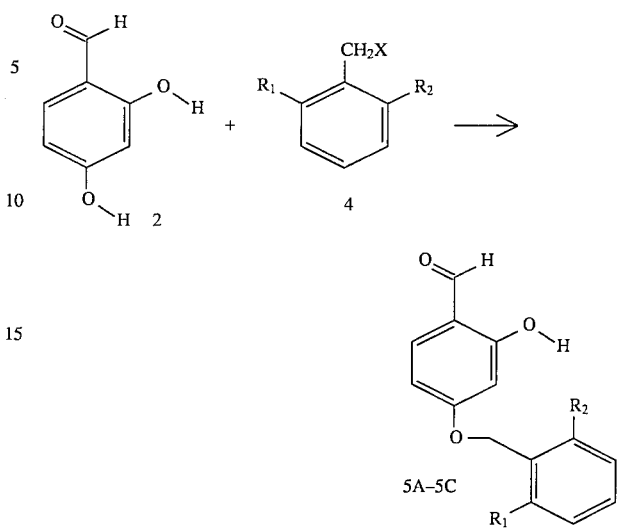

Scheme 7

TABLE II

| | Solution Assays of Alkylation by 4A–C[1]. (HPLC Area %) | | | | | |
|---|---|---|---|---|---|---|
| Electrophile | Method[1] | comp 2[2] | Product[2] 5A, B, C | Bis Side-Product 3 | Isolated Yield[3] | Melting Point[4] |
| 4A. $R_1 = R_2 = F$ $X = Br$ | NaHCO$_3$ | 8 | (5A) 81 | 10 | 53%[5] | 79–81° |
| 4B. $R_1 = Cl, R_2 = H$ $X = Cl$ | NaHCO$_3$ | 11 | (5B) 80 | 7 | 73% | 104–106° |
| 4B. $R_1 = Cl, R_2 = H$ $X = Cl$ | KF[6] | 15 | (5B) 78 | 6 | 60% | 107–108° |
| 4C. $R_1 = Me, R_2 = H$ $X = Cl$ | NaHCO$_3$ | 16 | (5C) 78 | 4 | 68% | 81–84° |

(1). All reactions in refluxing acetonitrile for 16 h. See experimental section.
(2). HPLC assay of reaction solution: PAR at 275 nm.
(3). Unless otherwise indicated product was crystallized from hexane/ethyl acetate. All products give satisfactory C, H, and halogen analysis (if applicable) (+/−0.4%).
(4). Uncorrected
(5). Removal of bis-ether required recrystallization from hexane/toluene/tert-butyl methyl ether (TBME) (70/25/5).
(6). Without KI catalyst Therefore, another aspect of the present invention is the the use of mild basic conditions, sodium bicarbonate or KF in refluxing acetonitrile, leads to an efficient, cost-effective, regioselective 4-benzylation of 2,4-dihydroxybenzaldehyde 1-Scheme 6).

In Scheme 8 below, a preferred aldehyde, shown herein as a 4-unsubstitutedbenzyloxy-2-hydroxy-benzaldehyde 6-Scheme-8, is converted to the chiral nitrone 7-Scheme-8. In step (a) of Scheme 8 tributylamine, triethylamine or DBU (1,8-diazabicylco[5,4,0]undec-7-one) in toluene may be used. Alternatively, p-toluene sulfonic acid and THF may be used as the catalyst in place of tributylamine or triethylamine. An alternative sugar moiety to the D- or L- mannose, such as a D- or L- Gulose may be used to form a similar oxime for condensation with the aldehyde obtaining a similar diastereomeric ratio but the gulose process is one step longer as the sugar moiety is only available as the gulonic lactone, and significantly more expensive for large scale process.

The nitrone 7-Scheme-8 is then cyclized into the benzofuran intermediate 8-Scheme-8 in a highly diastereoselective manner, such as in an 8:1 to 10:1 yield of the preferred diastereomer. This cyclization is accomplished using an ylide, such as dimethylsulfoxonium methylide [S(O)(CH$_3$)$_3$ (CH$_2$)], or (dimethylamino)phenyl-oxosulfoxnium methylide, such as the tetrafluorborate salt, preferably the ylide is S(O)(CH$_3$)$_3$ (CH$_2$). Yields of greater than 97% d.e. have been achieved using this method. The nitrone 7-Scheme-8 which now has a phenolic ortho-substitutent will undergo an intramolecular cyclization with elimination of a neutral thioether, leading to a benzodihydrofuran. This reaction creates in a single step, with high purity, a 2,3-dihydrobenzo [d]furan heterocycle having a chiral hydroxylamine substituent. The intramolecular cyclization process, using the and a solvent such as an alcohol in water, such as methanol, ethanol or isopropanol, preferably EtOH. It is further preferable that the pH of the reaction to remove the mannose is about 7. It has been found that for hydroxylamines having an R$_1$ moiety of an optionally substituted benzyloxy that the ratio of hydroxylamine to bicarbonate be in the order of 1:1 ratio, or preferably a slightly higher amount of hydroxylamine to base, i.e. 3.7 to 3.5 equivalents. A preferred amount is about 3.7 equivalents to 3.5 equivalents respectively, and the ratio of alcohol to water will range from about 1:1 to about 2:1, dependent upon the solubility of the R1 moiety, in particular an optionally substituted benzyl.

Scheme 8

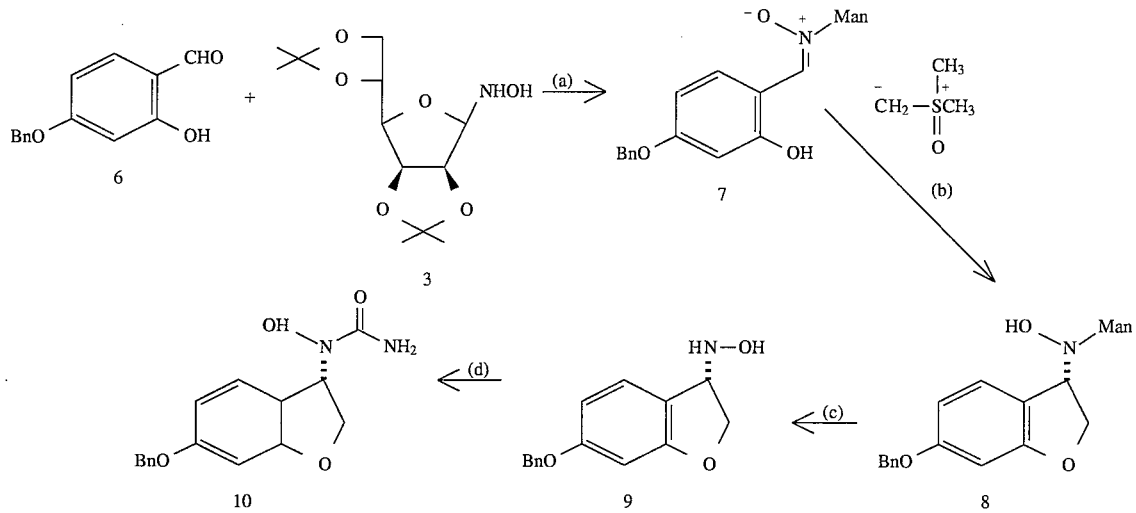

sulfoxide ylide described herein may be performed, in a variety of solvents, such as xylene, THF, or toluene. Toluene is the preferred solvent with a non-fluronitated nitrone substrate and THF is the preferred solvent with the fluorinated nitrone substrate.

The mannose auxiliary, such as on the compound of 8-Scheme-8, may readily be removed under mildly acidic conditions to yield the chiral hydroxylamine 9-Scheme-8 which may be convened to the desired final product, the hydroxyurea 10-Scheme-8, using art recognized procedures, and an appropriately substituted cyanate derivative, such as those described in WO 91/14674, published 10.03.91 to Adams et al., whose disclosure is incorporated by reference herein in its entirety, or as indicated in the working examples herein.

Removal of the chiral auxiliary from the resulting heterocyclic ring may result in removal of the entire hydroxylamine moiety and produce the undesirable by-product of a unsaturated bond, such as in the 2,3 position of the benzo [d]furan ring. Preferably, the condition used to selectively reduce the undesired byproduct are midly acidic condition, such as DMF and TFA; DMF/H$_2$O and hydrochloric acid, preferably 1N; CH$_3$CN and 1N HCl with or without water; DMF and 1N HCl; THF, water and 1N HCl, DMF, IPA and 1N HCl, DMF, alcohol, preferably methanol and 1N HCl; or DMSO, water and 1N HCl.

A preferred method for the removal of the chiral auxilary are reaction conditions which would allow recovery, and reuse of the sugar moiety. Such method uses in place of water, the reagent NH$_2$OH, preferably as the HCl salt. Also it is desirable to use in this reaction the reagent NaHCO$_3$, The compound 8-Scheme-8 may be displayed in its alternative short form, i.e. wherein the sugar moiety is abbreviated as mannose. The actual structure is as shown below and may be used in either manner herein.

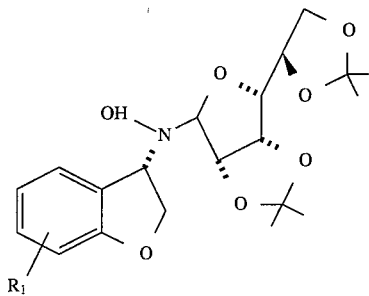

Similarly, the nitrone intermediate 7-Scheme-8 is also displayed in its alternative short form, i.e. wherein the sugar moiety is abbreviated as mannose. The actual structure is as shown below and may be used in either manner herein.

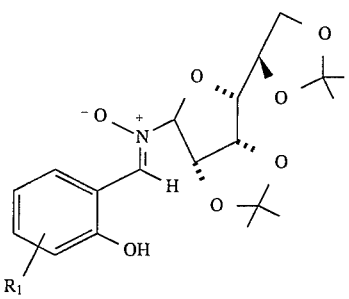

The tandem condensation-cyclization reaction between the dimethylsulfoxonium methylide and the mannose nitrone intermediate can be carried out in at least three different ways:

(1) One method is to separately generate the methylide from 1.0 eq of potassium tertbutoxide and 1.1 eq of trimethylsulfoxonium iodide in THF. The resulting methylide solution in THF is titrated with hydrochloric acid to the phenolphthalein endpoint (equivalent ratio 1:1). Exactly one equivalent of methylide is then added to a solution of mannose nitrone in THF. This is the preferred method of generation.

(2) One equivalent of potassium tert-butoxide can be added to the mannose nitrone in THF and the phenol moiety of the mannose nitrone is deprotonated. The solution is then treated with trimethylsulfoxonium iodide and the methylide is generated in situ with the phenolate anion of the substrate itself acting as the base. Because this in situ generation of the ylide requires temperatures above 30°–40° C., the reaction proceeds with lower diastereoselectivity than the first method illustrated above.

(3) An excess of methylide from trimethylsulfoxonium iodide (or trimethylsulfoxonium chloride) in DMSO can be generated using sodium hydride as base, or from trimethylsulfoxonium chloride in THF using sodium hydride as base, and then treating the resulting solution with the mannose nitrone. The excess methylide in the reaction mixture results in the formation of excess undesired side-products.

One aspect of the present invention is a process wherein the ylide is the used in an efficent one-pot, two-step diastereoselective synthesis for preparation of the hydroxylamine derivative from the nitrone intermediate. In greater detail, in the first step, the ylide is prepared by treating a slurry of trimethylsulfoxonium iodide (preferably in a 1.1 equivalent) in THF at room temperature with potassium tert-butoxide (preferably about 1.0 equivalent). The potassium tert-butoxide can either be added neat as a solid or as a solution in THF. Concentrations of potassium tert-butoxide of 0.40M in THF with respect to the iodide salt are preferable. Once the potassium tert-butoxide has been added, the reaction mixture is heated to about 40° C. The reaction can be monitored via the use of iminostilbene as the acid/base IPC indicator. Iminostilbene is deprotonated by potassium tert-butoxide, but not by the dimethyl-sulfoxonium methylide, as the dimethylsulfoxonium methylide is a much weaker base than potassium tert-butoxide. Aliquots of the reaction mixture can be taken at various intervals and treated with either solid iminostilbene crystals or with a solution of iminostilbene in THF. A solution of iminostilbene in THF is yellow in color while the corresponding deprotonated iminostilbene in THF is purple in color. The reaction is halted by removing the heat as soon as all the potassium tert-butoxide has been consumed. The reaction mixture is allowed to cool, preferably quickly cooled, to room temperature with stirring and then filtered through a plug of Celite to remove the potassium iodide, which is generated in the reaction, and the excess trimethylsulfoxonium iodide, such as indicated below.

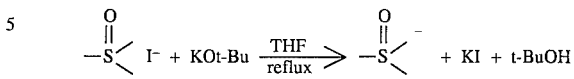

The filtrate consists of the ylide and an equimolar mount of tert-butanol in THF. The ylide/THF solution can then be titrated with hydrochloric acid to the phenolphthalein endpoint to determine its molarity; a method developed by Corey (Corey, E. J.; Chaykovsky, M. J. Am. Chem. Soc. 1965, 87, 1353).

In the second step there is a cyclization of the nitrone to form the dihydrofuran portion of the molecule with DMSO functioning as the leaving group.

This approach to forming the dimethylsulfoxonium methylide allows one to conveniently synthesize this ylide in THF from the relatively inexpensive trimethylsulfoxonioum iodide salt. Alternatively, one can generate this ylide in THF also using the more expensive trimethylsulfoxonium chloride salt, which is more soluble in THF than the iodide salt. While the chloride salt can be used as the starting material in THF, NaH is then the commonly employed base for deprotonation, as opposed to KOt-Bu. Deprotonation of the iodide salt in THF with NaH, however, generally does not occur because neither the salt nor the base are soluble enough in this solvent. Deprotonation of the iodide salt with NaH generally entails the use of DMSO as the reaction solvent where the iodide salt is completely soluble. The presence of DMSO, does however lower the diastereoselectivity of the initial condensation step of this one-pot, two-step reaction.

As indicated above, another method used to generate this ylide in THF involves the use of sodium hydride as a base with trimethylsulfoxonium chloride and also involves monitoring the reaction by observing the cessation of hydrogen gas evolution. One drawback to this method is that the cessation of hydrogen gas evolution, in large scale production of the ylide, is difficult to judge as the evolution is not uniform with respect to time.

Another aspect of the present invention is the use of potassium tert-butoxide as the limiting reagent and iminostilbene as the indicator to measure completion of the reaction process. This combination allows one to conveniently follow the course of this reaction with respect to the disappearance of the base. The reaction is stopped as soon as a color change is no longer seen with respect to the iminostilbene indicator.

Synthetic Examples

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

EXAMPLE 1

4-benzyloxy-2-hydroxybenzaldehyde

Preparation of 4-benzyloxy-2-hydroxybenzaldehyde: To solution of 2,4-dihydroxybenzaldehyde (160 g, 1.16 moles) in acetonitrile (2 L) was added potassium fluoride (134 g, 2.30 moles) and benzyl chloride (257 g, 2.03 moles). The reaction was heated to reflux and the volume of solvent was reduced by distillation to approximately half of original over the period of 24 hours. When less than 8% of starting material remains as observed by HPLC the residual acetonitrile is evaporated at reduced pressure and the residue was suspended in water. The aqueous mixture was extracted with ethyl acetate several times and the combined extracts were washed with potassium carbonate, hydrochloric acid and brine. Evaporation of the organic solvent at reduced pressure afforded the crude product in 76% yield. If needed, the product may be recrystallized from t-butyl methyl ether and hexane.

EXAMPLE 2

N-(2,3:5,6-Di-O-isopropylidene-α-D-mannofuranosyl) [2-hydroxy-4-(phenylmethoxy)phenyl]methanimine N-oxide a) To a solution of 4-benzyloxy-2-hydroxybenzaldehyde (24.9 g, 0.109 1 mol) and 2,3:5,6-di-O-isopropylidene-α-D-mannofuranose-hydroxylamine (30.0 g, 0.109 1 mol) in toluene (640 mL) at room temperature was added triethylamine (35.5 mL, 0.2553 mol). The reaction was heated to reflux for 18 hours and the water was removed via a Dean Stark trap. After the reaction was cooled to room temperature, hexane (300 mL) was added to facilitate crystallization. The mixture was further cooled to 10° C. and stirred for one hour. The product was filtered and dried (40° C., 15 mm Hg) to give 40.5 g (76.5% yield from two crops) of the desired nitrone as a pale-yellow powder. Mp 144.5°–145.5° C.; $[\alpha]_d^{20}=+7.85$ (c=1.0, CHCl$_3$); $^1$H NMR (CDCl$_3$, 400 MHz)δ7.50 (s, 1 H), 7.42–7.33 (m, 5 H), 6.98–6.96 (d, 1 H), 6.51–6.48 (m, 2 H), 5.47 (s, 1 H), 5.32–5.31 (d, 1 H), 5.06 (s, 2 H), 4.99–4.96 (m, 1 H), 4.65–4.62 (m, 1 H), 4.40 (m, 1 H), 4.12–4.09 (m, 2 H), 1.5 (s, 3 H), 1.47 (s, 3 H), 1.39–1.37 (d, 6 H). Anal. Calcd. for $C_{26}H_{30}NO_8$: C, 64.45; H, 6.24; N, 2.89. Found: C, 64.07; H, 6.37; N, 2.76.

b) In an alternative synthesis of the title compound using tributylamine instead of triethylamine:

To a solution of 4-benzyloxy-2-hydroxybenzaldehyde (91.4 g, 0.401 tool) and 2,3:5,6-di-O-isopropylidene-alpha-D-mannofuranose-hydroxylamine (100.0 g, 0.364 mol) in toluene (640 mL) at room temperature was added tributylamine (74.3 g, 0.401 mol). The reaction was heated to reflux for 6 hours and the water was removed via a Dean Stark trap. After the reaction was cooled to room temperature, heptanes (250 mL) was added to facilitate crystallization. The mixture was further cooled to 10° C., and stirred for one hour. The product was filtered, rinsed with heptanes (2×250 mL) and dried (40° C., 15 mm Hg) to give the desired nitrone, as a pale yellow powder. Isolated 165.0 g (98.7% w/w) corresponding to a corrected yield of 92.2%. Mp 144.5°–145.5° C., 'HNMR (CDCl$_3$, 400 MHz) 7.50 (s, 1 H), 7.42–7.33 (m, 5 H), 6.98–6.96 (d, 1 H), 6.51–6.48 (m, 2 H), 5.47 (s, 1 H), 5.32–5.31 (d, 1 H), 5.06 (s, 2 H), 4.99–4.96 (m, 1 H), 4.65–4.62 (m, 1 H), 4.40 (m, 1 H), 4.12–4.09 (m, 2 H), 1.5 (s, 3 H), 1.47 (s, 3 H), 1.39–1.37 (d, 6 H). Anal. Calcd. for $C_{26}H_{30}NO_8$: C, 64.45; H, 6.24; N, 2.89. Found: C, 64.07, H, 6.37; N, 2.76. $[\alpha]_D^{20}=+7.85$ (c=1.0, CHCl$_3$).

EXAMPLE 3

Preparation of Dimethylsulfoxonium Methylide in Tetrahydrofuran.

A. From the chloride salt: Following the general procedure of Corey, a 60% dispersion of sodium hydride in mineral oil (5.15 g, 129 mmol) was washed three times with hexane and the solvent was decanted. The flask was evacuated to remove the last traces of hexane. The vacuum was broken, trimethylsulfoxonium chloride (16.6 g, 129 mml) and dry THF (225 mL) were added, and the system was placed under nitrogen. The mixture was heated to reflux with stirring. After refluxing for 8 h, the milky white mixture was cooled to room temperature and the finely divided sodium chloride was allowed to settle to the bottom of the flask. This ylide solution was filtered to remove the sodium chloride and titrated with hydrochloric acid to the phenolphthalein endpoint (equivalent ratio 1:1); the concentration of the ylide in THF was found to be 0.586M. B. From the iodide salt: A suspension of trimethylsulfoxonium iodide (79.2 g, 0.360 mol) in THF (600 mL) was treated with potassium tert-butoxide (300 mL, 0.300 mol, a 1.0 M solution in THF). The resulting orange-yellow slurry was then heated to about 40° C. under nitrogen for 20 minutes. The resulting milky cream colored solution was cooled to room temperature, the potassium iodide was filtered, and the filtrate was titrated with hydrochloric acid to the phenolphthalein endpoint.

EXAMPLE 4

(S)-(+)-N-(2,3:5,6-Di-O-isopropylidiene-α-D-manno-furanosyl)[2,3-dihydro-6-(phenylmethoxy)-3-benzofuranyl]-N-hydroxylamine A solution of dimethylsulfoxonium methylide in THF (176 mL, 103 mmol, a 0.586M solution in THF) was added to a stirred solution of nitrone N-(2,3:5,6-di-O-isopropylidene-α-D-mannofuranosyl)[2-hydroxy-4-(phenylmethoxy)phenyl]-methanimine N-oxide, produced in accordance with Example 2 above (50 g, 103 mmol) in THF (500 mL) at 40° C. (Other reaction solvents include DMSO, DMF, TBME, and acetonitrile.) During the addition, the reaction mixture heated up to 45° C. After addition was complete, the reaction was stirred for 15 minutes at 50° C. The reaction mixture was then concentrated in vacuo. The residual yellow-gold solid was dissolved in ethyl acetate (500 mL), washed with water (2×250 mL), dried over magnesium sulfate, and filtered. The solution was then treated with silica gel to remove any sulfoxide side-product, filtered, and concentrated in vacuo. The crude product was recrystallized from toluene (250 mL) and hexane (400 mL) to afford the hydroxylamine as a cream-colored precipitate, 44.5 g (86.5% from three crops) as a 7.0 to 1 mixture of diastereomers. HPLC (Zorbax SBC8, $CH_3OH/H_2O/CH_3CN$/0.5M ammonium acetate 5.75:2.25:1:1, 1.5 mL/min): $t_R$ (major diasteromer) 17.8 min; $t_R$ (minor diasteromer) 15.3 min. For the major diasteromer: $[\alpha]_D^{20}=+18.9°$ (c=1.0, CHCl$_3$); $^1$H NMR (CDCl$_3$, 400 MHz) δ1.34 (s, 3 H), 1.39 (s, 3 H), 1.46 (s, 3 H), 1.49 (s, 3 H), 4.06–4.14 (m, 2 H), 4.30–4.36 (m, 2 H), 4.50 H), 4.55 (bs, 1 H), 4.68–4.74 (m, 1 H), 4.82–4.86 (m, 2 H), 4.92–4.95 (m, 1 H), 5.03 (s, 2 H), 6.46–6.55 (m, 2 H), 7.19–7.43 (m, 6 H); $^{13}$C NMR (CDCl$_3$, 100 MHz) δ162.48, 161.10, 136.85, 128.58, 127.97, 127.43, 126.40, 117.01, 112.34, 109.11, 107.67, 98.46, 97.13, 84.74, 84.59, 80.87, 73.84, 73.67, 70.29, 66.69, 65.27, 26.83, 26.04, 25.31, 24.38.

EXAMPLE 5

S)-(+)-N-[2,3-dihydro-6-(phenylmethoxy)-3-benzofuranyl]-N-hydroxyurea a) Preparation of: To a solution of the mannose-hydroxylamine of Example 4 above (10 g, 0.02 mol) in DMF (100 mL) was cooled in an ice bath to about 5 ° C. TFA (10 mL, 0.13 mol) and water (20 mL) was added to the stirred solution, the ice bath was removed and the mixture was stirred at ambient temperature for 5 h. The reaction was cooled to about 5 ° C. in an ice-bath and the pH was adjusted to about 4.7–4.9 by treatment with 50% NaOH (about 7.3 mL). A solution of potassium cyanate (2.4 g, 0.03 mol) in water (50 mL) was slowly added and stirring continued for 1 h. The precipitated product was filtered, washed with water (50 mL) and hexanes (40 mL) and dried at 40° C. in vacuo to yield a slightly yellow solid. (4.4 g, 73.3% yield, assay: purity 94.5 %w/w, 99.5% e.e.)

b) Recyrstallization ofS)-(+)-N-[2,3-dihydro-6-(phenylmethoxy)-3-benzofuranyl]-N-hydroxyurea A suspension of the crude compound, prepared in step (a) above (4.0 g, 0.013 mol) in DMF (24 mL) was heated to about 50°–55 ° C. and the clear solution was filtered. The solution was allowed to cool to about 35° C. and TBME (84 mL) was added slowly resulting in the formation of a white suspension which is stirred at about 5° C. for 1.5 h. The crystalline product is filtered, washed with TBME and dried at 40° C. in vacuo to yield the title compound. (3.5 g, 87.5% yield, assay: 99.5% w/w, 100% e.e.)

c) An alternative method for removal of the chiral auxiliary with 1N HCl To a solution of the mannose-hydroxylamine of Example 4 above (2.0 g, 4 mmol) in DMF (20 mL) and H$_2$O (4 mL) was cooled in an water bath (about 25° C.), 1N HCl (7.0 mL, 7 mmol) was added to the stirred solution in 50 min, then the water bath was removed and the mixture was stirred at ambient temperature for about 2 hours. The reaction was cooled to about 5° C. in an ice bath and the pH was adjusted to about 4.5 by treatment with 6 N NaOH (0.5 mL, 3 mmol) and HOAc (0.24 mL, 4.2 mmol). A solution of potassium cyanate (0.34 g, 4.2 mmol) in water (2 mL) was added in one portion and stirring continued at about 5° C. for 30 min. The reaction mixture was treated with water (16 mL) and the resulting alurry was stirred for 10 rain at about 5° C. The white precipitate which formed was filtered, washed with water (10 mL) and hexanes (20 mL) and dried at 40° C. in vacuo to yield a white solid (0.95 g, 79.2% yield, assay: 93.1% w/w, 90.4% ee).

EXAMPLE 6

Alternative Removal of the Sugar Auxiliary From a Hydroxylamine Intermediate with recovery of Auxiliary a) Mannose auxiliary removal with NH$_2$OH.HCl: To a solution of NaHCO$_3$(2.90 g, 34.5 mmol) in H$_2$O(60 mL) was slowly added NH$_2$OH.HCl (2.60 g, 37.4 mmol). The resulting solution was added to a suspension of mannose hydroxylamine prepared in step (b) Example 4 above, (5 g, 93.7% w/w, 9.4 mmol) in EtOH(60 mL). The resulting suspension was refluxed for about 1h 20 min (at refluxing temperature reaction mixture was clear solution), then cooled to room temperature. The white suspension was filtered, washed with H$_2$O(50 mL) and hexanes (50 mL), then dried at 40° C. in vacuo to yield a white solid (2.32 g, 96.0% yield, assay: 100.2% w/w, 98.6% ee).

b) Reisolation of the mannose oxime Above mother liquor from the filtration was concentrated to remove EtOH, and then extracted with AcOEt (3×75 mL). Combined AcOEt layers were washed with H$_2$O (70 mL), dried over MgSO$_4$, filtered, evaporated, and the residue was crystallized from AcOEt (6 mL)/hexanes (55 mL) to give 2,3:5,6-Bis-O-(1-methylethylidene)-D-mannose (E) oxime as a white solid (2.30 g, 89.5% yield, assay: 101.1% w/w).

EXAMPLE 7

(S)-(+)-N-[2,3-dihydro-6-(2,6-difluorophenylmethoxy)-3-benzofuranyl]-N-hydroxyurea a) Preparation of 4-(2,6-Difluoro)benzyloxy-2-hydroxybenzaldehyde A solution of 2,4-dihydroxybenzaldehyde (25.0 g, 0.1810 mol) and NaHCO$_3$ (16.7 g, 0.1991 mol) in acetonitrile (160 mL) was heated to 60° C. In a separate flask 2,6-difluorobenzyl bromide (36.7 g, 0.1774 mol) and potassium iodide (0.9 g, 5.4 mmol) was dissolved in acetonitfile (89 mL). Once the 2,4-dihydroxy-benzaldehyde solution reached 60° C. the 2,6-difluorobenzyl bromide solution was added and the reaction was heated to reflux. Reflux was continued until no 2,6-difluorobenzyl bromide remained after about 16 hours as indicated by HPLC. The reaction was cooled to room temperature; water (294 mL) was then added. The reaction was transferred to a separatory funnel and extracted with t-butyl methyl ether (294 mL). The organic layer was then washed with an aqueous K$_2$CO$_3$ solution (294 mL), followed by water (294 mL), an 5% aqueous citric acid solution (294 mL) and finally with brine (294 mL). The organic layer was then stripped down to afford a pale pink solid (54.6 g). The solid was taken up in a mixture of toluene (80 mL), TBME (11 mL) and hexane (239 mL) and heated to a solution. The hot solution was then filtered through a bed of Celite. The filtrate was then cooled gradually to room temperature at which time crystallization began. The solution was left at room temperature for two hours then cooled to 5° C. in a refrigerator for two hours before it was filtered. The pale pink solid was then dried @40° C., 20 mm Hg for 18 hours. Isolated 8.1 g (56.0% corrected yield) of 4-(2,6-Difluoro)benzyloxy-2-hydroxybenzaldehyde.

b) Preparation of 2,6-Difluoro-N-(2,3:5,6-Di-O-isopropylidene-α-D-mannofuranosyl)[2-hydroxy-4-(phenylmethoxy) phenyl]methanimine N-oxide To a solution of 4-(2,6-difluoro)benzyloxy-2-hydroxybenzaldehyde prepared in step (a) above,(10.0 g, 37.8 mmol) and 2,3:5,6 -di-O-isopropylidene-α-D-mannofuranose-hydroxylamine (11.45 g, 41.6 mmol) in toluene (76 mL) at room temperature was added triethylamine (7.7 g, 0.0416 mol). The reaction was heated to reflux for 6 hours and the water was removed via a Dean-Stark trap. After the reaction was cooled to room temperature, heptane (50 mL) was added to facilitate crystallization. The mixture was further cooled to 10° C., and stirred for one hour. The product was filtered and dried (40° C., 15 mm Hg) to give 18.0 g (89.0% corrected yield) of nitrone, (2,6-Difluoro-N- (2,3: 5,6- Di-O-isopropylidene-alpha-D-mannofuranosyl)[2-hydroxy-4-(phenylmethoxy) phenyl]methanimine N-oxide) as a pale yellow solid.

c) Preparation of Dimethylsulfoxonium Methylide in Tetrahydrofuran. A solution of potassium tert-butoxide (11.78 g, 0.105 mol) in THF (302 mL) at room temperature was treated with solid trimethylsulfoxonium iodide (26.6 g, 0.121 mol). The resulting cream-colored slurry was refluxed for 10 minutes. After cooling to room temperature, the heterogeneous reaction mixture was filtered through Celite to remove the potassium iodide. A sample of the filtered light bronze-colored solution was titrated with hydrochloric acid (5 mL, 0.487 mmol, a 0.0974M volumetric standard solution in water) to the phenolphthalein endpoint. The concentration of the ylide solution (total volume: 280 mL) was determined to be 0.326M; hence, the reaction afforded 91.2 mmol (86.9%)

of ylide. The ylide solution was then concentrated to a 2.68M solution in THF before use.

d) Preparation of (S)-(+)-N-(2,3:5,6-Di-O-isopropylidene-alpha-D-mannofuranosyl)[2,3-dihydro-6-(2,6-difluorophenylmethoxy)-3-benzofuranyl-N-hydroxylamine A solution of dimethylsulfoxonium methylide in THF, prepared in step (c) above (18.7 mL, 50.0 mmol, a 2.68M solution in THF) was added to a solution of 2,6-difluoro-N-(2,3:5,6-di-O-isopropylidiene-alpha-D-mannofuranosyl)[2-hydroxy-4-(phenylmethoxy)-phenyl]methanimine N-oxide (26.1 g, 50.0 mmol) in THF (231 mL) at −5° C. at such a rate that the reaction temperature never rose above 0° C. After addition was complete, the reaction temperature was raised to 10° C. and the reaction mixture was stirred at this latter temperature for 12 h. The reaction temperature was decreased to −5° C. and a solution of dimethylsulfoxonium methylide in THF (2.06 mL, 5.5 mmol, a 2.68M solution in THF) was again added at such a rate that the reaction temperature never rose above 0° C. The reaction temperature was increased to 10° C. and the reaction mixture was stirred for two hours at this latter temperature. The reaction mixture was diluted with TBME (500 mL) and washed with water (3×400 mL). The organic layer was concentrated in vacuo. The bronze-colored residue was dissolved in TBME (500 mL), treated with silica gel, and passed through a plug of silica gel. The filtrate was concentrated in vacuo. A solution containing the crude material was then used in the next step without further purification.

e) Preparation of (S)-6-[(2,6-Difluorophenyl)methoxy]-2,3-dihydro-N-hydroxy-benzofuran-3-amine Hydroxylamine hydrochloride (10.12 g, 146 mmol) was slowly added to a solution of sodium bicarbonate (11.3 g, 134 mmol) in water (65 mL). The resulting hydroxylamine solution was added to a solution of crude mannose difluoro-hydroxylamine of step (d) above [(S)-(+)-N-(2,3:5,6-Di-O-isopropylidene-alpha-D-manno-furanosyl)[2,3-dihydro-6-(2,6-difluorophenyl-methoxy)-3-benzofuranyl-N-hydroxylamine](about 21 g as an 88:11:1 mixture of crude mannose difluoro-hydroxylamine, the diastereoisomer of crude mannose difluoro-hydroxylamine, and a sulfoxide side-product; about 34.5 mmol of the desired diastereomer) in ethanol (65 mL). The resulting heterogeneous solution was refluxed for 1.5 h (Note: After 30 rain of refluxing, the reaction mixture became totally homogeneous) and then cooled to room temperature and sitrred for another 1.5 h. The resulting cloudy yellow colored slurry was treated with water (110 mL) and stirred for 10 minutes. The yellow precipitate which formed was filtered, washed with water (220 mL), hexanes (220 mL), and then dried at 40° C. in vacuo to afford 12.55 g (80.4% w/w assay, 82% ee, 63% yield over two steps of the desired enantiomer) of the title hydroxylamine and its enantiomer as a yellow solid.

f) Preparation of (S)-N-Hydroxy-N-[2,3-dihydro-6-(2,6-difluorophenyl-methoxy)-3-benzofuranyl]urea: Acetic acid (3.51 mL, 61.4 mmol) was added to a solution of hydroxylamine (S)-6-[(2,6-Difluorophenyl)methoxy]-2,3-dihydro-N-hydroxybenzofuran-3-amine produced in accordance with step (e) above, and its enantiomer (12.0 g, 80.4% w/w assay, 82% ee, 29.9 mmol of the desired enantiomer) in DMF (73 mL) at room temperature. The reaction mixture was cooled in an ice bath to about 5° C. A solution of potassium cyanate (5.0 g, 61.4 mmol) in water (9 mL) was then added at such a rate that the reaction temperature never rose above 15° C. After addition was complete, the reaction mixture was stirred at about 5° C. for 30 min. The reaction mixture was treated with water (208 mL) and the resulting slurry was stirred for 1 h at 20°–25° C. The light yellow precipitate which formed was filtered, washed with water (200 mL), washed with hexanes (200 mL), and dried at 40° C. in vacuo to afford 11.11 g (89.3% w/w assay, 74% ee, 73% yield of the desired enantiomer) of crude hydroxyurea and its enantiomer.

(g) Recrystallization of (S)-N-Hydroxy-N-[2,3-dihydro-6-(2,6-difluorophenyl-methoxy)-3-benzofuranyl]urea. A suspension of the crude hydroxyurea produced in accordance with step (f) above, and its diastereomer (10.9 g, 89.3% w/w assay, 74% ee, 21.4 mmol of the desired enantiomer) in absolute ethanol (136 mL) was heated to a homogenous solution and then refluxed for 10 rain, filtered, and then slowly cooled to room temperature over a period of 2 h without stirring. The crystalline product was filtered, washed with hexanes (100 mL), and dried at 40° C. in vacuo to afford 6.6 g (90.6% recovery, 99.8% w/w assay, 99% ee) of the desired titled hydroxyurea enantiomer as a white solid.

EXAMPLE 8

2,3:5,6-Di-O-isopropylidene-D-mannose (E)-oxime
Preparation of 2,3:5,6-Di-O-isopropylidene-D-mannose (E)-oxime: D-Mannose (100 g, 0.555 mol) is added in three portions to a mixture of DMF (70 mL), dimethoxypropane (121.3 g, 1.166 mol) and p-toluenesulfonic acid (0.21 g, 1.11 mmol). The reaction is heated to 70°–80° C. for 1 hour or until the reaction is complete. The reaction mixture is cooled to room temperature. In a separate flask the $NH_2OH \cdot HCl$ (96.4 g, 1.39 mol) is added to a 10% NaOH solution (44.4 g, 1.11 mol in 444 mL water) and stirred for 15 minutes. This solution is then added to the vessel containing the diacetonide 2-Scheme-1 mixture. The reaction is heated to 80°–90° C. for 1 hour or until all starting material is consumed. The mixture is cooled to 5°–10° C. for 2 hours during which time crystallization occurs. The white solid is filtered and dried in a vacuum oven. (m.p. 144.5°–145.5° C.).

EXAMPLE 9

2,4-Dihyroxybenzaldehye

General Procedure for Vilsmeier-Haack reaction:

Oxalyl chloride (98%) and phosphorous oxychloride (99%) are obtained from Aldrich Chemical Co. and used without further purification. HPLC grade Baker Analyzed acetonitrile and Burdick & Jackson DMF are also used as received. $^1H$ and $^{13}C$ NMR spectra are taken in DMSO-d6 (unless otherwise indicated) on a Bruker AM-300 or a Bruker AR 360 spectrometer with TMS as the internal standard. Analytical HPLC (reverse phase) is carried out by dissolving about 0.05 ml of the reaction mixture in 50 ml of mobile phase and warming to 45° C. for 5 min and then sonicating for 3 min. This treatment totally converts salts 3-Scheme 4 or 4-Scheme 4 to the corresponding aldehyde 2,4-dihydroxybenzaldehye. HPLC conditions: Column: Bakerbond, 25 cm×4.6 mm i.d.; Solvent: acetonitrile: water: TFA 20:80:0.1; Flow rate: 0.8 mUmin, uv detection at 275 nm.

Method A. Vilsmeier-Haack reaction with phosphorus oxychloride:

A 1-L3 neck flask equipped with a temperature thermocouple and an overhead stirrer is charged with DMF (49.3 g, 0.675 mole) and acetonitrile (150 mL). The flask is treated with $POCl_3$ (88.16 g, 0.575 mole) in acetonitrile dropwise over 20 rain so that the temperature is maintained at 22°–28° C. with a water bath. The is stirred at ambient temperature for 1 h to insure complete conversion to the Vilsmeier reagent. The solution remains clear throughout. The reaction is cooled in a dry-ice bath to −14° to −17° C. and a solution of resorcinol (55.06 g, 0.5 mole) in acetonitrile (150 mL) is slowly added to maintain -10° to −17° C. during the addition. Precipitation of the Vilsmeier formamidinium-phosphoro-dichloridate 3-Scheme 4, occurs during this addition. The reaction is stirred for an additional 2 h at −15±2° C. and then at 28°–32° C. for 1 h. The HPLC of the reaction solution shows <5% of the starting material. (A small amount of an unknown with similar retention time to the 2,4-dihyroxybenzaldehye is present.) The reaction is cooled to 5° C. and after 1 h the product is isolated by filtration and rinsed with cold acetonitrile. The product is dried at 30° C. at 10 mm of Hg to constant weight. The light yellow solid, 123 g has a mp 158°–159° C.; HPLC wt/wt assay of 98.3% by hydrolysis to the title compound in the HPLC mobile phase. The corrected yield is 80%. The product can be stored in the dark at 5° C. for several weeks without significant coloration. FT-IR (KBr) (cm$^{-1}$) 3421, 3300–2350 (O-H, C-H, P-OH stretch), 1654 and 1642 (C=N stretch), 1617, 1582, 1473, 1346, 1323, 1311, 1262 and 1187 (P=O stretch, free/bonded, and C-O stretch), 1109 and 1077 (P-O-C stretch), 868, 834, 791,541 and 494 (P-Cl vibrations); $^1$H NMR (DMSO-$_{d6}$) δ11.3–11.5 (br, 2 H, O-H) (may appear as 2 discrete signals depending upon sample concentration), 8.81 (s, 1 H, CH=N), 7.67 (d, 1 H, J=9.07 Hz), 6.71 (d, 1H, J=2.22 Hz), 6.52 (dr, 1 H, J=9.03 and 2.22 Hz), 3.69 (s, 3H, C=N-CH$_3$), 3.58 (s, 3 H, C=N-CH$_3$); $^{13}$C NMR (DMSO-$_{d6}$) δ167.0, 164.2, 163.7, 133.1, 109.5, 106.4, 102.4, 50.2, 43.3.

Hydrolysis of 3-Scheme 4: To water (680 mL) stirred at 40° C. is added the above salt 3-Scheme 4 (122.6 g) in three portions. The reaction is heated to 52° C. for 0.5 h, and the reaction is cooled. When the temperature had reached 35° C., sodium thiosulfate solution (0.09M, 1–2 mL) is added to discharge the resulting pink color. The reaction is cooled to 5° C., and stirred for 2 h. The mixture is filtered, the solid is washed with cold water, and air dried for several hours. Vacuum drying at 30° C. at 0.05 mm of Hg yielded an off-white solid, 53.1 g, mp 134°–136° C. $^1$H NMR (CDCl$_3$) δ11.41 (s, 1H, O-H); hydrogen bonded), 9.70 (s, 1H, O=C-H), 7.42 (d, 1H, 6.47; ABX, J$_{AB}$=8.5 Hz), 6.47 (dd, 1H, ABX; J$_{BA}$=8.5 Hz, J$_{BX}$=2.3 Hz), 6.373 (d, 1H, ABX; J$_{BX}$=2.3 Hz), 5.7 (br.s, 1H, O-H); $^{13}$C NMR (CDCl$_3$)δ194.5, 164.4, 163.3 136.1, 115.6 108.6, 103.2. Analysis: Calc'd for C$_7$H$_6$O$_3$: C, 60.87; H, 4.38. Found: C, 60.34; H, 4.18.

Method B. Vilsmeier-Haack reaction with Oxalyl Chloride:

A 1–L 3 neck flask equipped with a temperature thermocouple and an efficient overhead stirrer is charged with DMF (46.37 g, 0.63 mole) and acetonitrile (350 mL). The reaction is treated dropwise with a solution of oxalyl chloride (66.12 g, 0.521 mole) in actionitrile dropwise over 20 min so that the temperature is maintained at 20°–26° C. with a water bath. Gas evolution is noted and a thick precipitate forms. The reaction is stirred at ambient temperature for 1 h to insure complete conversion to the Viismeier reagent. The reaction is cooled in a dry-ice bath to −14° to −17° C. and a solution of resorcinol (26.87 g, 0.244 mole) in acetonitrile (75 mL) is added over 20 min. The Viismeier reagent dissolves as the reaction with resorcinol occurs, and soon afterward the precipitation of chloride salt 4—Scheme 4 begins. The reaction is stirred at −15° C. for 35 min, then at 28°–32° C. for 2 h. The HPLC of the reaction solution shows <6% of the starting material. A small amount (3–4% by area) of the same unknown seen in the above example with similar retention time to the title compound is present. After cooling to 3°–5° C. for 2 h, the reaction is filtered and washed with cold acetonitrile (70 mL). The solid is washed with hexane (30–40 mL) and the product dried. The Vilsmeier formamidinium chloride is dried at 30°–35° C. at 0.05 mm of Hg for 24 h. The recovery is 42.3 g; the yield corrected for purity is 79%; it is a single component by HPLC, mp 170°–173° C. FT-IR (KBr) (cm$^q$) 3414 (O-H stretch), 3000–3100, 2576, 1644/1615/1584/1472 (C=N stretch), 1356, 1317 1242, 1217, 1146, 980, 882, 749, 721,646, 492. The carbon and proton NMR of the chloride are the same as the spectra of the phosphorodichloridate salt prepared above. Analysis: Calc'd for C$_9$H$_{12}$ClNO$_2$: C, 53.61; H, 6.00; Cl, 17.58; N, 6.95. Found: C, 53.38; H, 6.02; Cl, 17.54; N, 6.80.

Hydrolysis of 4-Scheme 4:

The above salt 4-Scheme 4(42.3 g, 0.209 mole) is hydrolyzed in water (0.25 L) at 50° C. as described above for 3-Scheme 4. After filtration, the product is dried at <35 ° C for 24 h giving 1 (24.4 g, wt/wt assay by HPLC 97%; corrected yield: 69% from 2-Scheme 4). The melting point, proton and carbon NMR of this product are identical to that of the product produced by the POCl$_3$ sequence.

EXAMPLE 10

Benzylation of 2,4-dihydroxybenzaldehyde

Benzyl chloride (99%) and potassium fluoride (spray-dried, 99%) were obtained from Aldrich Chemical Co. and used without further purification. 2,4-Dihydroxybenzaldehyde was purchased from Fluka Co. and used as received, or prepared by method indicated in Example 9 above. Sodium bicarbonate (powder) was obtained from J. T. Baker. Potassium fluoride (Aldrich, 99%) was further dried in vacuo at 80° C. for 16 h before use. HPLC grade Baker Analyzed acetonitrile, ethyl acetate, and hexane are used as purchased. tert-Butyl methyl ether (TBME) was obtained from Burdick & Jackson. $^1$H NMR and $^{13}$C NMR were recorded in DMSO-d$_6$ on a Broker AM-300 or a Bruker AR 360 spectrometer with TMS as the internal standard. Analytical HPLC (reverse phase) wass done on an Ultrasphere ODS column, 25 cm×4.6 mm i.d. (5μ); mobile phase acetonitrile:water: TFA 60:40:0.1; Flow rate 1.3 mL/min; uv detection at 275 nm.

General Procedure: Preparation of 4-Benzyloxy-2-hydroxybenzaldehyde (1-Scheme 7) using Sodium Bicarbonate:

A 2–L 3 neck flask equipped with a temperature thermocouple and an overhead stirrer is charged with 2,4-dihydroxybenzaldehyde (103.59 g, 0.75 mole, 1 eq), sodium bicarbonate powder (71.83 g, 0.855 mole, 1.14 eq), potassium iodide (12.45 g, 0.075 mole, 0.1 eq), and acetonitrile (700 mL). The reaction is heated to 60° C. and benzyl chloride (123.43 g, 0.975 mole, 1.30 eq) is added over 1 min. The reaction is stirred and heated at reflux until the PAR (% area response) of 2,4-dihydroxybenzaldehyde is 4–6% by HPLC assay. The solvent is removed in vacuo, and the solution is treated with water (260 mL), concentrated hydrochloric acid (12 mL), and ethyl acetate (500 mL, at 30° C.). The layers are separated, and the aqueous layer extracted with additional ethyl acetate (150 mL). The organic layers are combined and washed successively with 3% aqueous potassium carbonate saturated with ethyl acetate (2 times), water, 5% aqueous citric acid, and brine. The organic layer is evaporated in vacuo (rotovap). The residue is dissolved by heating in TBME (500 mL) at 40°–50° C. and on cooling to 30° C., hdxane (620 mL) is added. The resulting precipitate is stirred for 2 h at 5°–10° C., and the product collected by filtration. The flask is rinsed with cold TBME-hexane (200 mL of a 1:1 (v/v) mixture). After air drying for 1.5 h, the product is dried at <35° C. for 16 h (10 mm of Hg.). The product, 126.2 g, produced an HPLC wt/wt assay of 93.1% compared to a purified standard; the corrected yield is 69%; mp 76°–78° C. $^1$H NMR (DMSO-$d_6$)$\delta$11.06 (s, 1 H, phenolic O-H), 10.0 (s, 1 H, CHO), 7.62 (d, 1 H, J=8.54 Hz), 7.33–7.45 (m, 5 H, aryl-H), 6.60–6.64 (2 d, 2H), 5.15 (s, 2H, ARCH$_2$), 3.39 (H$_2$O). $^{13}$C NMR (DMSOd$_6$)$\delta$190.9, 164.9, 163.0, 136.2, 132.1, 128.5, 128.1, 127.8, 116.3, 107.9, 101.7, 69.6. The HPLC shows the major peak (7.2 rain) and the presence of 2–4% (PAR) of the late running (17.5 rain) 2,4-bis-benzyloxybenzaldehyde (3-Scheme 7) (peak confirmed by co-elution with an authentic sample (Reimann, E., Chem. Ber., 1969, 102, 2881.).

Preparation of 4-Benzyloxy-2-hydroxybenzaldehyde using Potassium Fluoride:

A 5-L 3 neck flask equipped with a temperature thermocouple and an overhead stirrer is charged with 2,4-dihydroxybenzaldehyde (160.2 g, 1.16 mole, 1 eq), dry potassium fluoride (134.1 g, 2.30 mole) and acetonitrile (1.6 L). The reaction is stirred and heated; when the temperature reaches 55° C., benzyl chloride (257.0, 2.03 mole) is added in a single portion with a small volume of acetonitrile as a rinse. The reaction is refluxed and stirred for 16–21 h, at which time the PAR of starting material (retention time 2.3 rain) is <8%. Most of the acetonitrile is removed by distillation (15 mm of Hg) over 40 minutes at 40°–45° C. and the residue is treated with water (6.0 L) and ethyl acetate (2.5 L). The layers are separated, and the aqueous layer extracted with additional ethyl acetate (2×2.2 L). The organic layers are combined and washed successively with 3% aqueous potassium carbonate (3% v/v, saturated with ethyl acetate), water (2 L containing 12 mL of concentrated hydrochloric acid), and brine (2 L). The organic layer is evaporated in vacuo (rotovap). The resulting crude solid is dried in a vacuum oven at 30° C. for 12 h and 4 the product is dissolved by stirring and heating in TBME (750 mL at 45°–50° C. and on cooling to 30° C., hexane (950 mL) is added. The resulting precipitate is stirred for 2 h at 5°–10° C., and the product collected by filtration. The flask is rinsed with cold TBME-hexane (350 mL of a 1:1 (v/v) mixture). After air drying for 1.5h, the product is dried at <35° C. for 16 h (10 mm of Hg). The product 200 g, gives an HPLC wtw assay of 88% of a purified standard; corrected yield is 67%; mp 75–77° C. Elemental analysis: Calc'd for $C_{14}H_{12}O_3$: C, 73.67; H, 5.30. Found C, 73.41; H, 5.30. The HPLC shows the major peak (7.2 rain) and the presence of 1–3% (PAR) of the late running (17.5 min) 2,4-bis-benzyloxybenzaldehyde. All spectral data of title compound were identical to an authentic sample prepared above.

Preparation of 5A, 5B, and 5C as described in Table II

The above alkylation procedures are carded out on 2,4-dihydroxybenzaldehye replacing benzyl chloride with 2,6-difluorobenzyl bromide, 2-chlorobenzyl chloride, and 2-methylbenzyl chloride to give 5A, 5B, and 5C-Scheme 7 respectively. The reactions are conducted in the usual manner and after 16 h at reflux, the solution product ratios are examined by HPLC. The work-up is the same as above, and the products are characterized by elemental analysis and proton and carbon NMR. The isolated yields are determined after one crystallization with the exception of 4A-Scheme 7 to produce 5A-Scheme 7. The product 5A-Scheme 7 required a second crystallization from hot hexane/toluene/TBME to satisfactorily remove the bis-benzyl byproduct. This product was analyzed as >98% by C, H, F analysis and by HPLC against a reference standard.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for proudcing 2,4-dihydroxybenzaldhyde which process comprises
    a) adding oxalyl chloride, acetonitrile and DMF to form a reaction mixture;
    b) reacting resorcinol with the reaction mixture to yield the compound

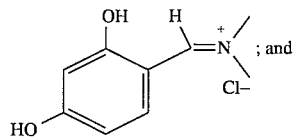

; and b) adding water to form 2,4-dihydroxy-benzylaldehyde.

2. A compound of the formula

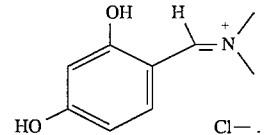

3. A process for producing 2,4-dihydroxybenzaldhyde which process comprises
    a) adding POCl$_3$, acetonitrile, and DMF to form a reaction mixture;
    b) reacting resorcinol with the reaction mixture to yield the compound

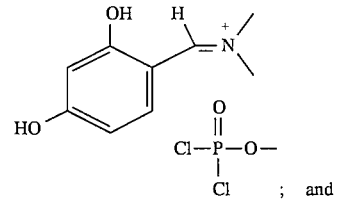

; and b) adding water to form 2,4-dihydroxy-benzylaldehyde.

4. A compound of the formula:

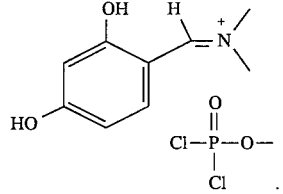

* * * * *